United States Patent [19]

Hjerten et al.

[11] Patent Number: 4,725,343

[45] Date of Patent: Feb. 16, 1988

[54] HIGH PERFORMANCE ELECTROPHORETIC MOBILIZATION OF ISOELECTRICALLY FOCUSED PROTEIN ZONES

[75] Inventors: Stellan Hjerten, Uppsala, Sweden; Ming-De Zhu, Beijing, China

[73] Assignee: Bio-Rad Laboratories, Inc., Richmond, Calif.

[21] Appl. No.: 787,291

[22] Filed: Oct. 15, 1985

[51] Int. Cl.$^4$ .............................. G01N 27/26
[52] U.S. Cl. ................. 204/183.2; 204/182.9
[58] Field of Search .............. 204/183.2, 182.1, 182.9, 204/180.1, 299 R, 182.8

[56] References Cited

U.S. PATENT DOCUMENTS 3,692,654 9/1972 Svendsen ...................... 204/183.2

OTHER PUBLICATIONS

Boddin, M. Hilderson, H. J. Lagrou, A. Dierick; W. "Preperative Isoelectric Focusing-Eluction of the Gradient Without Interrupting the Electric Field", Analytical Biochemistry, (97, vol. 6491), pp. 293-296.
Racusen et al., "Preparative Electrophoresis on Polyacrylamide Gel," *Analytical Biochemistry*, 7, 62–66 (1964).
Jovin et al., "An Apparatus for Preparative Temperature-Regulated Polyacrylamide Gel Electrophoresis," *Analytical Biochemistry*, 9, 351–369 (1964).
Arlinger et al., "Boundary Sharpness in Capillary-Tube Isotachophoresis Demonstrated by UV Detection," *Science Tools, The LKB Instrument Journal*, 17, (1), 21–23 (1970).

*Primary Examiner*—John F. Niebling
*Assistant Examiner*—John S. Starsiak, Jr.
*Attorney, Agent, or Firm*—Townsend and Townsend

[57] ABSTRACT

Protein zones which have been isoelectrically focused in a separation medium are mobilized for analytical or preparative purposes by changing the anolyte, catholyte or both to provide these two solutions with pH's varying in the same direction from the isoelectric points of each of said protein zones, then applying a voltage between them. The focused protein zones then elute as a unit from the separation medium while substantially maintaining their same positions relative to each other without hydrodynamic flow through the medium itself. Mobilization is alternatively achieved by hydrodynamic flow, for instance by pumping the focused protein zones with voltage maintained to suppress zone distortion (due to the hydrodynamic flow) and zone broadening (due to diffusion).

10 Claims, 6 Drawing Figures

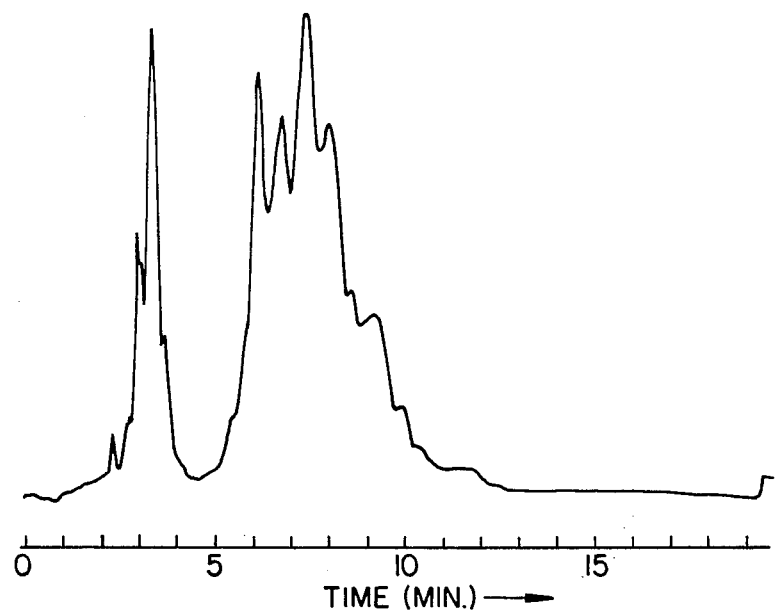
FIG._1.
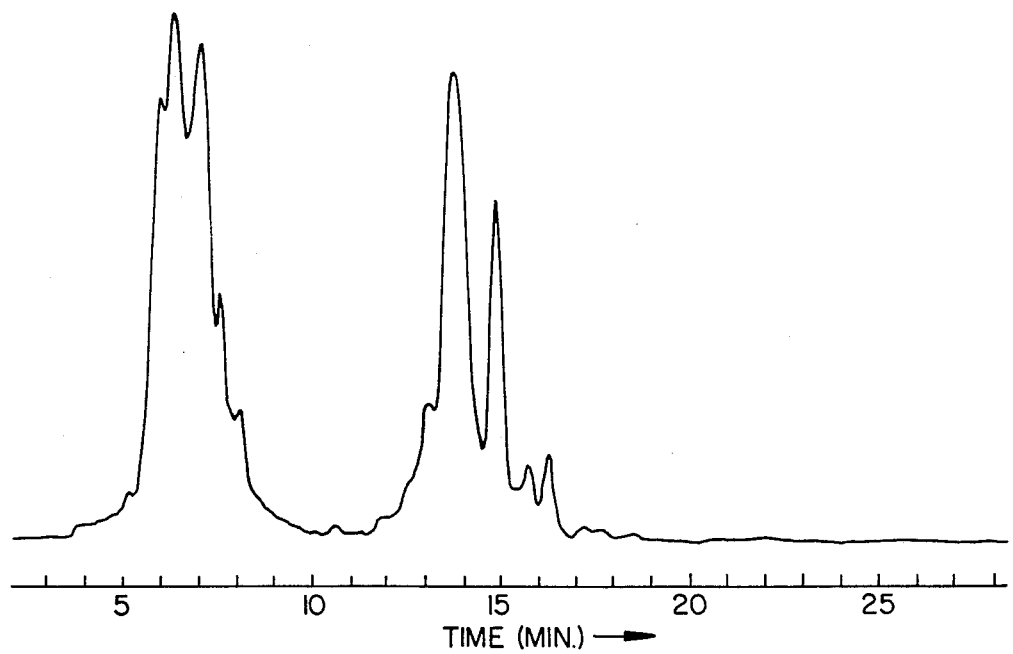
FIG._2.

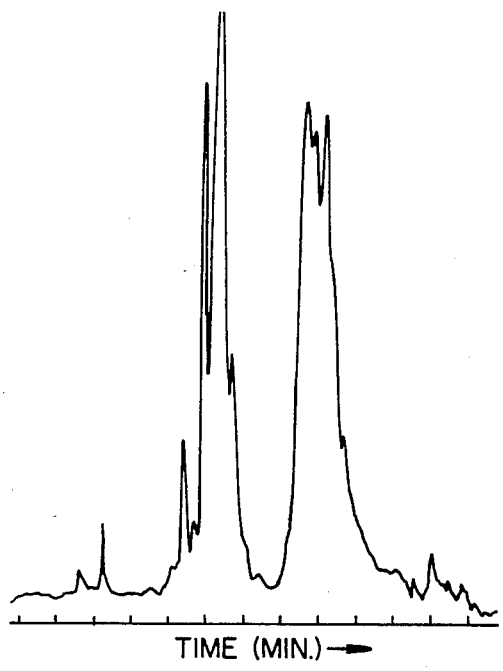
FIG._3.
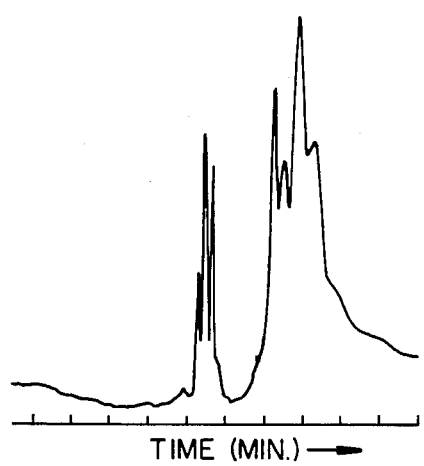
FIG._5.
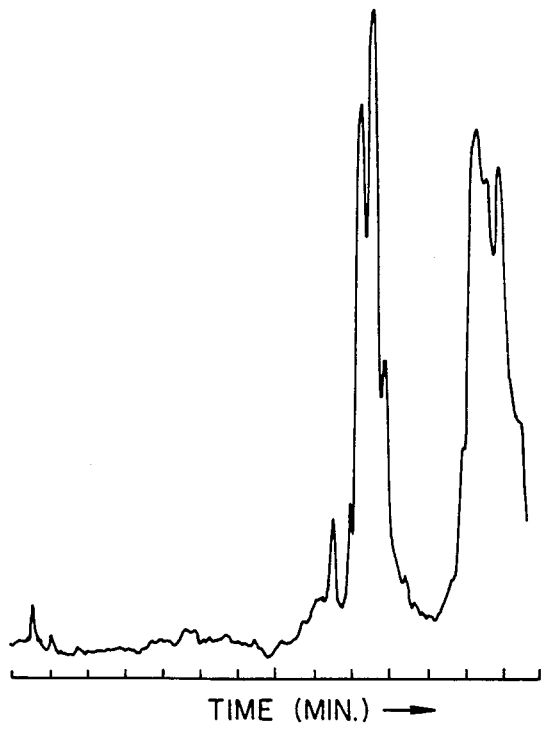
FIG._4.

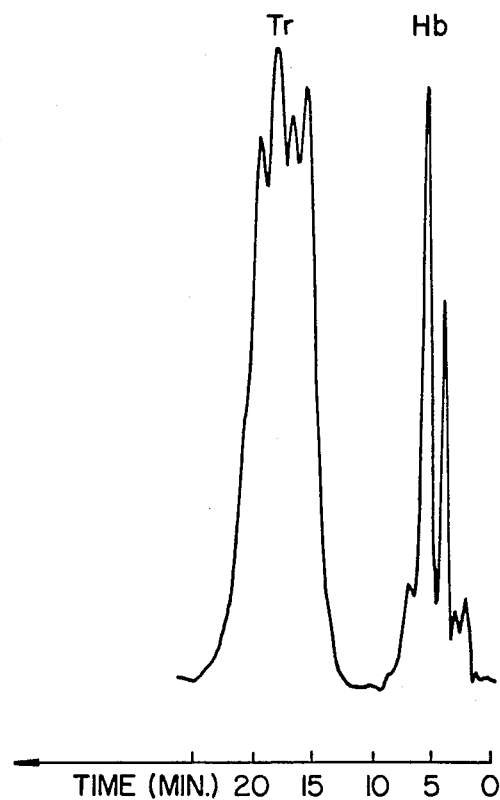
FIG._6.

HIGH PERFORMANCE ELECTROPHORETIC MOBILIZATION OF ISOELECTRICALLY FOCUSED PROTEIN ZONES

BACKGROUND OF THE INVENTION

This invention relates to isoelectric focusing, and partioularly to methods for mobilizinq a foousod pattern of protein zones in a separation medium for purposes of recovery, detection or both.

High performance liquid chromatography (HPLC) is popular for both analytical and small scale preparative purposes, due to its ability to provide both high speed and high resolution of very small samples. Electrophoresis, including isoelectric focusing, may also be done on a small scale, with similar advantages of speed and resolution.

To achieve speeds similar to those obtainable in HPLC systems, electrophoresis-based systems must use detection techniques which avoid staining and derivatization. The most suitable techniques are light absorption measurements, done either by scanning the medium in which the zones are focused, or by mobilizing the focused zones past a single detection point in the medium itself or out of the medium into a detection cuvette.

Mobilization has the advantage of not requiring motorized scanning equipment. It further enables one to recover the isolated zones individually for preparative purposes. Mobilization by pumping a solution through the tube or other vessel in which the medium is held to purge the vessel by hydrodynamic flow has previously been used following isoelectric focusing in sucrose gradients (without voltage applied). In this case, the parabolic zone distortion caused by the pumping is suppressed by the sucrose gradient, although zone broadening by diffusion still occurs. This way of suppressing zone distortion only works when the column has relatively large diameter, for instance 3-20 mm, and only when mounted in a vertical position. For narrow-bore columns (diameters in the range 0.05-2 mm) sucrose gradients will not suppress the parabolic zone distortion occurring during the pumping procedure. Mobilization of isoelectrically focused zones by pumping cannot, of course, be used when the focusing is performed in a gel.

SUMMARY OF THE INVENTION

New mobilization methods for protein zones which have been isoelectrically focused in a separation medium have now been developed. According to one embodiment of the invention, once steady state has been achieved by isoelectric focusing, either the anolyte or the catholyte or both are changed such that both have pH's varying in the same direction from the isoelectric points of each of the protein zones. A voltage is then applied between the two and consequently across the separation medium, to move the entire pattern of protein zones as a unit while the medium itself remains stationary. The process may be used for the preparative recovery of the protein bands as they emerge from the medium, as well as for analytical purposes, either by passing the bands across a single detection point in the medium itself or through an external detector. Zone broadening occurs to a lesser degree in this method than in the pumping method used for sucrose gradient columns without voltage referred to above.

According to another embodiment of the invention, the mobilization is achieved by pumping and with voltage applied during the pumping. This method has the advantage over the previously used pumping procedure that the column can be mounted in any direction, for instance horizontally, and that both the parabolic zone distortion, caused by the pumping, and the distortion caused by diffusion are efficiently suppressed and that no sucrose gradients are required for suppressing the parabolic zone distortion.

BRIEF DESCRIPTION OF THE DRAWINGS

FIG. 1 is a strip-chart recorder trace from an ultraviolet absorption detector, representing the separation of human hemoglobin from human transferrin by one embodiment of the process of the invention.

FIG. 2 is a repeat of the experiment shown in FIG. 1, using a second embodiment of the present invention.

FIG. 3 is a comparative recorder trace generated by a prior art scanning technique.

FIG. 4 is a recorder trace taken from the same separation system used for FIG. 3 and using the same scanning technique except, however, that the anolyte was changed sometime prior to the scanning so that the zones had migrated a certain distance.

FIG. 5 is a recorder trace from a separation similar to that of FIG. 1, except that a gel rather than a liquid solution was used as the separation medium.

FIG. 6 is a recorder trace from an experiment where the mobilization was achieved by pumping with voltage applied during the whole mobilization procedure.

DETAILED DESCRIPTION OF THE INVENTION

Separation media to which the present invention is applicable include all media in which proteins can move under the influence of an electrical field and can be focused in discrete zones by isoelectric focusing. Such media may include liquids, gels and suspensions. Liquid media are generally preferred. Depending on the pH gradient maintained during the focusing, the separation medium will contain an appropriately selected electrolyte, preferably an ampholyte, to promote the focusing. The separation medium may assume any physical configuration which will permit the separation of proteins into zones along a single longitudinal axis. Preferred configurations will be those which avoid the accumulation of heat generated by the electrical current, so as to minimize the distortion of the zones during both focusing and mobilization. Thin-walled, thin diameter capillary tubes are preferred, particularly when on-line detection is used. Particularly useful are glass tubes whose inner walls have been coated with methyl cellulose to eliminate zone distortion due to electroendosmosis and the adsorption of solutes by the glass wall The isoelectric focusing may be done according to conventional methods, involving the combination of an electric field and a pH gradient. The pH gradient preferably runs from an anolyte which is acid or neutral to a catholyte which is neutral or basic. In particularly preferred embodiments, the anolyte is an acidic aqueous solution and the catholyte is a basic aqueous solution. Isoelectric focusing is continued until a steady state is achieved—i.e., until a movement of proteins in the separation medium is substantially stopped.

Mobilization is then achieved by changing the pH of either the anolyte or the catholyte or both, so that both have pH's which vary in the same direction from the isoelectric points of each of the protein zones —i.e., both have pH's either above or below the isoelectric point(s) of the substance(s) to be mobilized. Preferably, the change is made to provide both with the same pH. This is most conveniently done by replacing one of these solutions with the other. Once the change is made, a voltage is applied across the separation medium with the result that the entire pattern of focused protein zones moves as a unit out of the medium. The voltage may be adjusted during the mobilization so that the protein bands travel with a minimum of distortion from their steady state forms and relative positions. Thus, conditions are adjusted as necessary to approach as closely as possible a purely translational motion of the protein zone pattern with respect to the stationary separation medium.

Alternatively, one of the solutions may be replaced with water. When voltage is then applied and mobilization occurs, the pH at the water end of the tube will change continuously but will always be higher (when the anolyte has been replaced) or lower (when the catholyte has been replaced) than the isoelectric point(s) of the particular protein(s) being eluted.

As an optional variation of these embodiments, a solution may be pumped through the tube containing the separation medium to supplement the driving force imposed by the voltage.

When the separation medium is a liquid rather than a gel or a suspension, mobilization may be achieved without changing either the anolyte or catholyte, but by merely pumping the liquid out of the column in which isoelectric focusing took place. This is done while a voltage is applied, the voltage being any voltage high enough to maintain the sharpness of the bands. Preferably, the voltage is at least as great as that used during the isoelectric focusing.

Mobilization is done either to draw all of the protein bands past a preselected detection point in the medium for purposes of on-line detection, or to move the bands out of the medium entirely for purposes of external detection or preparative recovery of the individual proteins. Detection may be achieved by any conventional method such as, for example, light absorption techniques.

The following examples are offered for illustrative purposes only, and are intended neither to define nor limit the invention in any manner.

EXAMPLE 1

A glass tube measuring 120 mm in length, having an inner diameter of 0.2 mm and a wall thickness of 0.1 mm was coated with methyl cellulose by rinsing with an aqueous solution of 0.4 g methyl cellulose in 100 ml of distilled water to which had been added 7 ml of formic acid and 35 ml of formaldehyde, draining for 5 minutes, and finally placing in an oven at 120° C. for 40 minutes. The tube was then filled with a 1% solution of Pharmalyte TM (an ampholyte obtained from Pharmacia Fine Chemical, Uppsala, Sweden) containing human transferrin obtained from KABI/Vitrum, Stockholm, Sweden, and hemoglobin prepared from outdated human erythrocytes. The tube was then placed in an isoelectric focusing apparatus using 0.02 M phosphoric acid as the anolyte and 0.02 M sodium hydroxide as the catholyte. An agarose gel plug was inserted in the cathodic end of the tube. For detection, a prism monochromator focused a narrow beam of a wavelength of 280 nm across a segment of the tube near one end. A photomultiplier was arranged to intercept the beam after passing through the tube. Its output was recorded on a strip-chart recorder.

A voltage of 1200 volts was applied across the tube. Focusing as evidenced by visual inspection of the hemoglobin zones was completed within twenty minutes. The phosphoric acid in the anode vessel was then replaced with 0.02 M sodium hydroxide and a voltage of 3000 volts was applied. The current rose from an initial value of 14 microamps to about 30 microamps as the last peak was recorded. Elution was completed in about ten minutes. The recorder output is shown in FIG. 1, wherein the two largest peaks in order of elution are hemoglobin and transferrin.

The experiment was repeated except that the sodium hydroxide in the cathode vessel was replaced with 0.02 M phosphoric acid after focusing, rather than vice versa. Elution was completed in about seventeen minutes, and the recorder output is shown in FIG. 2, the transferrin eluting first.

To determine the extent of alterations in the protein pattern during the mobilization of the protein zones, the experiment was repeated, using a free zone electrophoresis apparatus for detection, in accordance with Hjerten, "Free Zone Electrophoresis," *Chromatographic Reviews*, 9:122 at p. 147 et seq. (1967), whereby the focusing is done in a horizontal tube which is slowly rotated around its long axis to avoid zone spreading due to gravity, and detection is done by scanning the length of the tube. The recorder output after the isoelectric focusing is shown in FIG. 3, with the hemoglobin on the left side of the trace. The acid at the anode was then replaced by the base as before to cause elution, and detection was repeated, again by scanning the length of the tube. The recorder output as shown in FIG. 4 when the transferrin zone had migrated to a position close to the anodic end of the tube.

EXAMPLE 2

The experiment of Example 1 was repeated, using, however, a polyacrylamide gel as the separation medium rather than an ampholyte solution. The recorder output is shown in FIG. 5.

EXAMPLE 3

The focusing step was performed as in Example 1, but the mobilization step was achieved by pumping with voltage (3000 volts) applied (see FIG. 6).

The foregoing description is offered primarily for purposes of illustration. Numerous modifications and variations of the procedures and materials described above, while still falling within the spirit and scope of the invention as claimed hereinbelow, will be readily apparent to those skilled in the art.

What is claimed is:

1. A method for the mobilization of a pattern of protein zones in an elongate separation medium in which said protein zones have been isoelectrically focused, said separation medium bridging an anolyte at a first pH and a catholyte at a second pH different from said first pH, said method comprising (a) changing at least one member selected from said anolyte and said catholyte to provide said anolyte and said catholyte with pH's varying in the same direction from the isoelectric points of each of said protein zones, and (b) applying a voltage between said anolyte and said catholyte of sufficient intensity to cause translational motion of said pattern with respect to said medium.

2. A method in accordance with claim 1 in which step (a) comprises changing only one member selected from said anolyte and said catholyte.

3. A method in accordance with claim 1 in which step (a) comprises changing said anolyte only.

4. A method in accordance with claim 1 in which step (a) comprises changing said catholyte only.

5. A method in accordance with claim 1 in which step (a) comprises providing said anolyte and said catholyte with substantially the same pH.

6. A method in accordance with claim 1 in which step (a) is performed by exchanging said catholyte for water.

7. A method in accordance with claim 1 in which step (a) is performed by exchanging said anolyte for water.

8. A method in accordance with claim 1 in which the voltage of step (b) is of the same polarity as that under which said protein zones have been isoelectrically focused.

9. A method in accordance with claim 1 in which said anolyte is an acidic solution and said catholyte is a basic solution, and step (a) comprises replacing said anolyte with said catholyte.

10. A method in accordance with claim 1 in which said anolyte is an acidic solution and said catholyte is a basic solution, and step (a) comprises replacing said catholyte with said anolyte.

* * * * *